United States Patent
Litvak

(10) Patent No.: US 7,149,583 B1
(45) Date of Patent: *Dec. 12, 2006

(54) METHOD OF USING NON-SIMULTANEOUS STIMULATION TO REPRESENT THE WITHIN-CHANNEL FINE STRUCTURE

(75) Inventor: Leonid M Litvak, Los Angeles, CA (US)

(73) Assignee: Advanced Bionics Corporation, Valencia, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 10/819,609

(22) Filed: Apr. 7, 2004

Related U.S. Application Data

(60) Provisional application No. 60/461,553, filed on Apr. 9, 2003.

(51) Int. Cl.
*A61N 1/18* (2006.01)
(52) U.S. Cl. .................. 607/57; 607/137; 381/316
(58) Field of Classification Search ............... 607/57, 607/137; 381/316
See application file for complete search history.

(56) References Cited

U.S. PATENT DOCUMENTS

| | | |
|---|---|---|
| 3,751,605 A | 8/1973 | Michelson |
| 4,400,590 A | 8/1983 | Michelson |
| 4,495,384 A | 1/1985 | Scott et al. |
| 4,819,647 A | 4/1989 | Byers et al. |
| 5,603,726 A | 2/1997 | Schulman et al. |
| 5,626,629 A | 5/1997 | Faltys et al. |
| 5,938,691 A | 8/1999 | Schulman et al. |
| 6,052,624 A | 4/2000 | Mann |
| 6,067,474 A | 5/2000 | Schulman et al. |
| 6,078,838 A | 6/2000 | Rubinstein |
| 6,129,753 A | 10/2000 | Kuzma |
| 6,157,861 A | 12/2000 | Faltys et al. |
| 6,195,585 B1 | 2/2001 | Karunasiri et al. |
| 6,205,360 B1 | 3/2001 | Carter et al. |
| 6,208,882 B1 | 3/2001 | Lenarz et al. |
| 6,219,580 B1 | 4/2001 | Faltys et al. |
| 6,249,704 B1 | 6/2001 | Maltan et al. |

(Continued)

FOREIGN PATENT DOCUMENTS

WO  WO-00/01200 A1  1/2000

(Continued)

OTHER PUBLICATIONS

McDermott, et al., "Pitch Ranking with Nonsimultaneous Dual-Electrode Electrical Stimulation of the Cochlea", J Acoust Soc Am, vol. 96(1), (1994) pp. 155-162.

(Continued)

*Primary Examiner*—Angela D. Sykes
*Assistant Examiner*—Alyssa M. Alter
(74) *Attorney, Agent, or Firm*—Philip H. Lee

(57) ABSTRACT

The present invention provides a cochlear stimulation system and method for capturing and translating FTS in incoming sounds and delivering this information spatially to the cochlea. An embodiment of the system may comprise an FTS estimator/analyzer and a current navigator. An embodiment of the method of the invention can comprise: analyzing the incoming sounds within a time frequency band, extracting the slowly varying frequency components and estimating the FTS to obtain a more precise dominant FTS component within a frequency band. After adding the fine structure to the carrier to identify a precise dominant FTS component in each frequency band (or stimulation channel), a stimulation current is steered to the precise spatial location on the cochlea that corresponds to the dominant FTS component, the steering accomplished by delivering non-simultaneous stimuli through at least two electrodes.

21 Claims, 7 Drawing Sheets

U.S. PATENT DOCUMENTS

| | | | |
|---|---|---|---|
| 6,289,247 | B1 | 9/2001 | Faltys et al. |
| 6,295,467 | B1 | 9/2001 | Kollmeier et al. |
| 6,393,325 | B1 | 5/2002 | Mann et al. |
| 6,415,185 | B1 | 7/2002 | Maltan |
| 2003/0167077 | A1* | 9/2003 | Blamey et al. ............... 607/57 |
| 2004/0136556 | A1* | 7/2004 | Litvak et al. ............... 381/316 |

FOREIGN PATENT DOCUMENTS

| | | |
|---|---|---|
| WO | WO-02/09808 A1 | 2/2002 |
| WO | WO-03/015863 A2 | 2/2003 |

OTHER PUBLICATIONS

Rubinstein et al., "The Neurophysiological Effects of Simulated Auditory Prosthesis Simulation" Second Quarterly Progress Report NO1-DC-6-2111.

van Wieringen, et al., "Comparison of Procedures to Determine Electrical Stimulation Thresholds in Cochlear Implant Users", Ear and Hearing, vol. 22(6), (2001), pp. 528-538.

Zeng, et al., "Loudness of Simple and Complex Stimuli in Electric Hearing", Annals of Otology, Rhinology & Laryngology, vol. 104 (9), (1995) pp. 235-238.

Zhang, et al., "Loudness of Dynamic Stimuli in Acoustic and Electric Hearing", J Acoust Soc Am, vol. 102(5) Pt. 1, (Nov. 1997), pp. 2925-2934.

Overstreet, Litvak, and Faltys Inventors for AB-378U; U.S. Appl. No. 10/698,097, filed Oct. 31, 1003; entitled "Multi-Electrode Stimulation to Elicit Electrically-Evoked Compound Action Potential."

Litvak, Krubsack, and Overstreet, inventors for AB-354U; U.S. Appl. No. 10/712,078, filed Nov. 13, 2003; entitled "Method and System to Convey the Within-Channel Fine Structure with a Cochlear Implant."

Harnsberger, et al., "Perceptual "vowel spaces" of Cochlear Implant Users: Implications for the Study of Auditory Adaptation to Spectral Shift", J. Acoust. Soc. Am., vol. 109(5), pt. 1, (May 2001), pp. 2135-2145.

Morse, et al., The Practical Use of Noise to Improve Speech Coding by Analouge Cochlear Implants, Chaos, Solutions and Fractals, vol. 11, No. 12, (2000) pp. 1885-1894.

Scheirer, et al., "Construction and Evaluation of a Robust Multifeature Speech/Music Discriminator", Acoustics, Speech, and Signal Processing (1997), IEEE International Conference in Munich, Germany (Apr. 21-24, 1997), pp. 1331-1334.

Smith et al., "Chimaeric Sounds Reveal Dichotomies in Auditory Perception", Nature, vol. 416, No. 6876, (Mar. 7, 2002), pp. 87-90.

\* cited by examiner

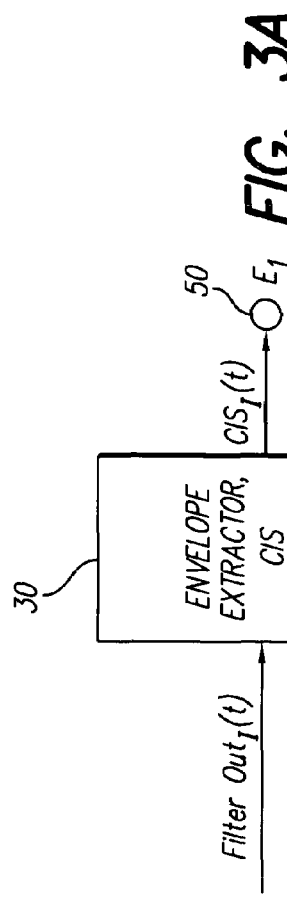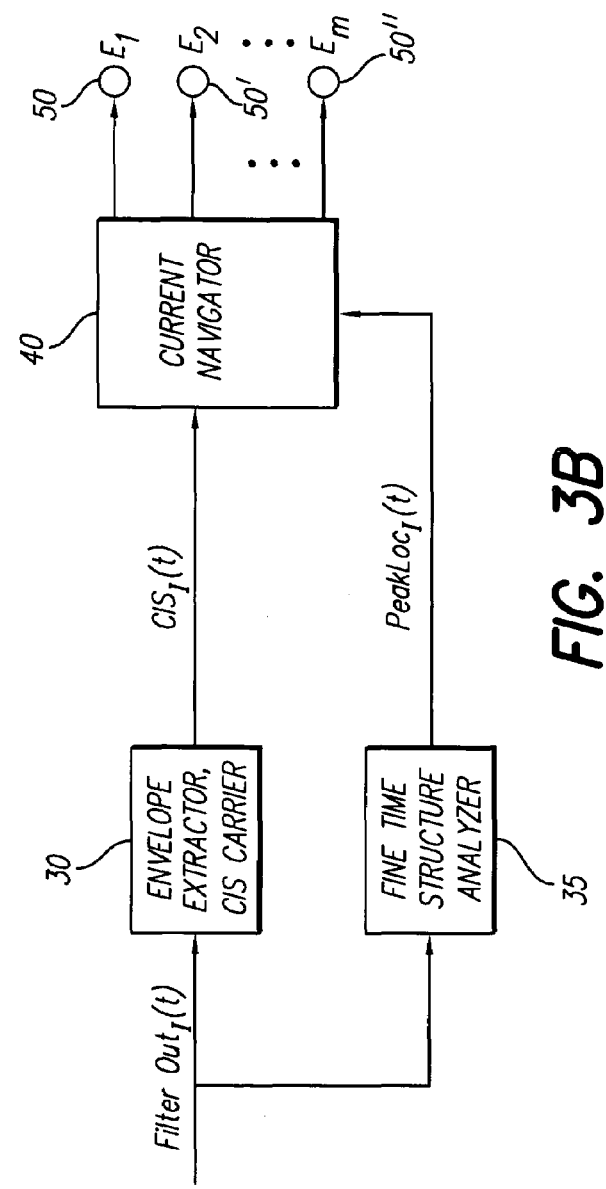

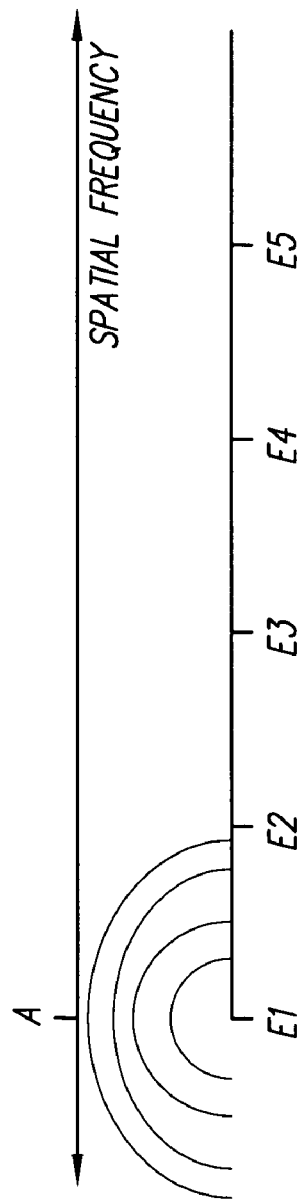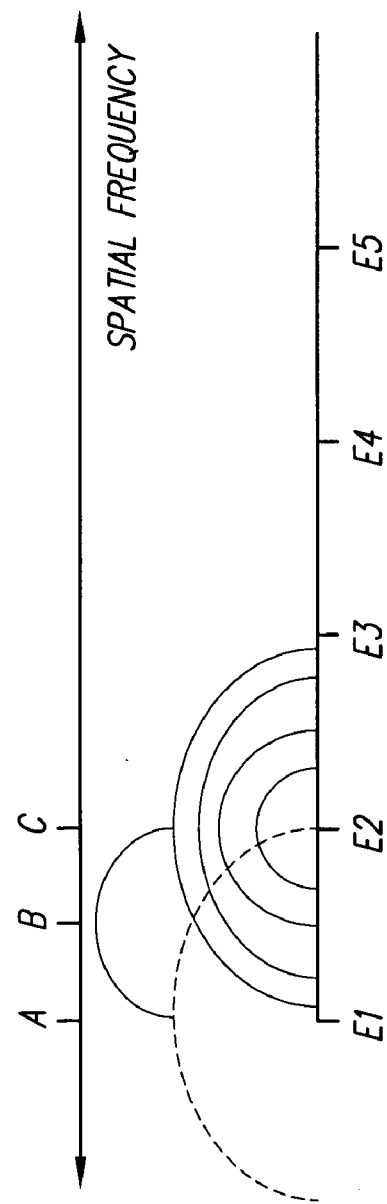

METHOD OF USING NON-SIMULTANEOUS STIMULATION TO REPRESENT THE WITHIN-CHANNEL FINE STRUCTURE

The present application claims the benefit of U.S. Provisional Patent Application Ser. No. 60/461,553, filed 9 Apr. 2003, which application is herein incorporated by reference in its entirety.

BACKGROUND OF THE INVENTION

The present invention relates to systems and methods for stimulating the cochlea. More specifically, the present invention relates to systems and methods of stimulating the cochlea for representing fine time structure in incoming sounds.

Fine time structure ("FTS") is the fast varying information present in sounds. The FTS has been shown to be essential for recognition of musical melodies, as well as for finely discerning other sounds.

In conventional, pulsatile, continuous interleaved sampler ("CIS") strategy, the incoming sound is broken into a small number of frequency bands, for example, between 8 to 22 bands. A more complete description of an exemplary cochlear implant system is found in U.S. Pat. No. 6,219,580, incorporated herein by reference. Conventionally, the slowly-varying envelope is extracted from each band and this envelope information is used to modulate a high-frequency pulsatile carrier signal that is presented to a multiplicity of stimulating electrodes. In this conventional method of processing sound, some of the FTS information is discarded, namely, the fast-varying components present in each frequency band or stimulation channel.

FTS can be conveyed to the auditory nerve fibers in two different ways: (a) temporally, with respect to the discharge patterns of the auditory nerve fibers over time; and (b) spectrally, with respect to the cochlear excitation pattern over the length of the cochlea. Because different segments of the cochlea, over its length, are associated with different sound frequencies, the spatial location on the cochlea represents the spectral frequencies of the incoming sounds. It is unclear which of the two modes of variation, temporal or spectral, is more important for conveying the FTS.

In a conventional CIS system, the use of discrete electrodes fixes the position of the electrical stimulation field emanating from each electrode. Thus, if eight electrodes are used, there are eight dominant, but fixed, stimulation points on the cochlea. Spatial points on the length of the cochlea, which are between electrodes and between the dominant stimulation points, are poorly stimulated because only those areas closest to the electrodes are well stimulated. As a result, the conventional system can not accurately convey the FTS spatially to the cochlea.

It would be desirable to capture the FTS in incoming sounds and to deliver this information with improved spatial accuracy over the length of the cochlea. In addition, it would be desirable to achieve these results employing a stimulator system that is not capable of simultaneously delivering separately controlled current pulses through at least two electrodes, i.e., the pulse amplitude delivered from each electrode cannot be varied independently.

What is needed, therefore, is a method and system of processing auditory sound waves into electrical signals that captures FTS information and accurately directs this information to appropriate nerves that spatially innervate the cochlea.

SUMMARY OF THE INVENTION

The present invention addresses the above and other needs by providing a stimulation strategy that accurately conveys the FTS.

In one embodiment of the present invention, a cochlear stimulation system is provided for capturing and delivering fine time structure (FTS) in incoming sounds. The system comprises: an electrode array, having a multiplicity of electrodes placed into the cochlea; a stimulator having a multiplicity of stimulation channels connected to the electrode array, said each channel represented by a window or band of frequencies; an envelope extractor for extracting a slowly varying frequency envelope in the incoming sound; an FTS analyzer for estimating the FTS information within a frequency band, the analyzer contained within the stimulator; and a current navigator, which uses the identified dominant FTS component at each band of frequency and steers the stimulation to each point of the cochlea that spatially corresponds to the identified dominant FTS component. The current navigator employs non-simultaneous stimulation, such that a first stimulus at a first electrode is followed immediately by a second stimulus at a second electrode in order to produce stimulation steering.

In another embodiment of the present invention, a cochlear stimulation method is provided for capturing and delivering FTS in incoming sounds, wherein the stimulation is provided by a multiplicity of electrodes in an electrode array connected to a multi-channel stimulator. An embodiment of the method comprises: analyzing the incoming sounds within frequency windows or bands, each frequency band representing one channel; extracting the slowly varying frequency carrier component of the incoming sound in each frequency band with an envelope; estimating the dominant FTS component using an FTS analyzer; adding the dominant FTS component to the carrier component to provide a precise corresponding spatial location on the cochlea; and steering the stimulation current to the precise spatial location on the cochlea using a current navigator and non-simultaneous stimulation.

The present invention employs a non-simultaneous method of stimulation, which can "steer" a resulting stimulation as if it is spatially emanating somewhere between a first electrode and a closely placed second electrode. This non-simultaneous stimulation method comprises delivering a stimulus pulse at the first electrode, followed shortly by delivery of a second pulse at the second electrode. This non-simultaneous method can produce a perceived sound frequency which is spectrally somewhere between what would normally be perceived in response to a single stimulus emanating from either the first electrode or second electrode alone.

The non-simultaneous method of stimulation steering is particularly suited for performing stimulation navigation when the stimulator hardware does not provide independent programming capability, e.g., to deliver different current stimulus amplitudes at the same time to two different electrodes. The non-simultaneous method of the present invention enables stimulation navigating (steering) in such a stimulator system, provided that the system can deliver the second stimulus pulse sufficiently quickly after the first pulse to be within the refractory period of the target nerve.

It is a feature of the invention to provide two methods for analyzing the FTS which involve: (1) within a predetermined time interval, for a particular frequency band or window, averaging the intervals between the zero crossings of an incoming sound wave and calculating the dominant FTS component or (2) in a predetermined time interval, using a Fast Fourier Transform to deconstruct a sound wave, in order to identify the dominant FTS component in each particular frequency band or window.

It is a further feature of the present invention that capturing FTS and conveying this information to corresponding places on the cochlea may be performed employing non-simultaneous stimulation through two or more electrodes in conjunction with additional concepts such as M of N stimulation strategies.

BRIEF DESCRIPTION OF THE DRAWINGS

The above and other aspects, features and advantages of the present invention will be more apparent from the following more particular description thereof, presented in conjunction with the following drawings wherein:

FIG. 3A shows a block functional diagram representing conventional sound processing in a cochlear implant using an envelope extractor;

FIG. 3B shows, in accordance with the present invention, a block functional diagram representing the present invention, which includes an FTS analyzer/estimator and a current navigator;

FIG. 6A shows a five electrode array and a representation of the activation curve around electrode, E1, which activation curve results from a first applied stimulus, S1;

FIG. 6B shows the same electrode array depicted in FIG. 6A. E2 is the second electrode and is shown with a representation of the activation curve resulting from a second stimulus, S2.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
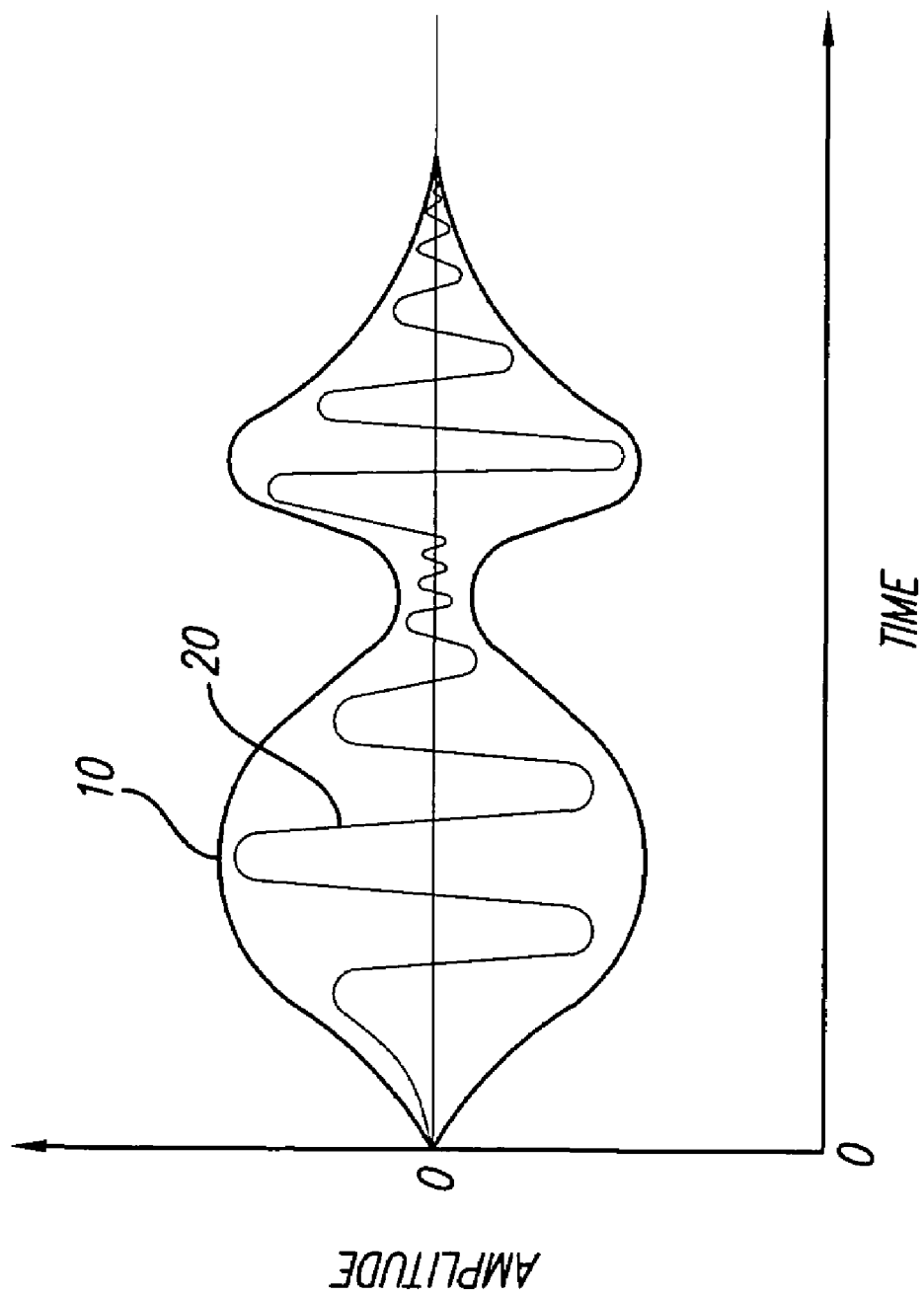
FIG. 1 shows a representation of sound wave amplitudes as a function of time and a slowly moving envelope.

FIG. 1 shows a representation of incoming sound waves as a function of time. The envelope 10 of the sound provides the slow moving or lower frequency components of the sound. The faster varying components of the incoming sound 20 are the FTS components of the sound. Conventional cochlear stimulation systems take the incoming sounds, as represented in FIG. 1, and deconstruct the sounds into frequency bands (windows), as shown in FIGS. 2A and 2B.

Figure 2A:
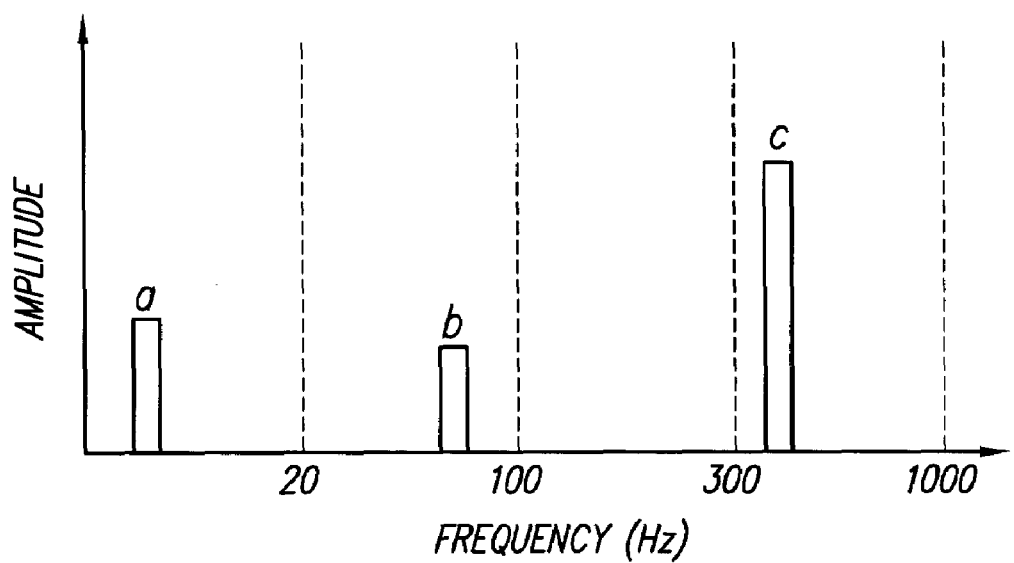
FIG. 2A shows a graph depicting four frequency bands or windows with dominant FTS components a, b and c.

FIG. 2A provides an example in which incoming sounds are processed into four separate frequency bands or windows. In this example, the four frequency bands may represent four distinct stimulation channels. To implement the four channels, at least four stimulating electrodes are generally required to convey the necessary stimuli to the cochlea. The dominant FTS components a, b and c occur in three of four frequency bands shown. Minor peaks may be present but are not illustrated here, as they are ignored in processing. The third frequency band does not show any activity.

In conveying the identified, dominant FTS in each band, the stimulation system delivers stimulation pulses to three of four electrodes that are placed on the cochlea. The specific amplitudes of each dominant FTS component can be translated as perceived sound intensities. These perceived sound intensities can be increased by increasing the stimulation amplitude of a pulse such that more nerve fibers are recruited (captured) at one time. In addition, the frequency of the train of pulses delivered at the electrode can also recruit more nerve fibers within a fixed time interval. Such an increase in pulse frequency and amplitude can translate to an increase in perceived, sound intensity.

Figure 2B:
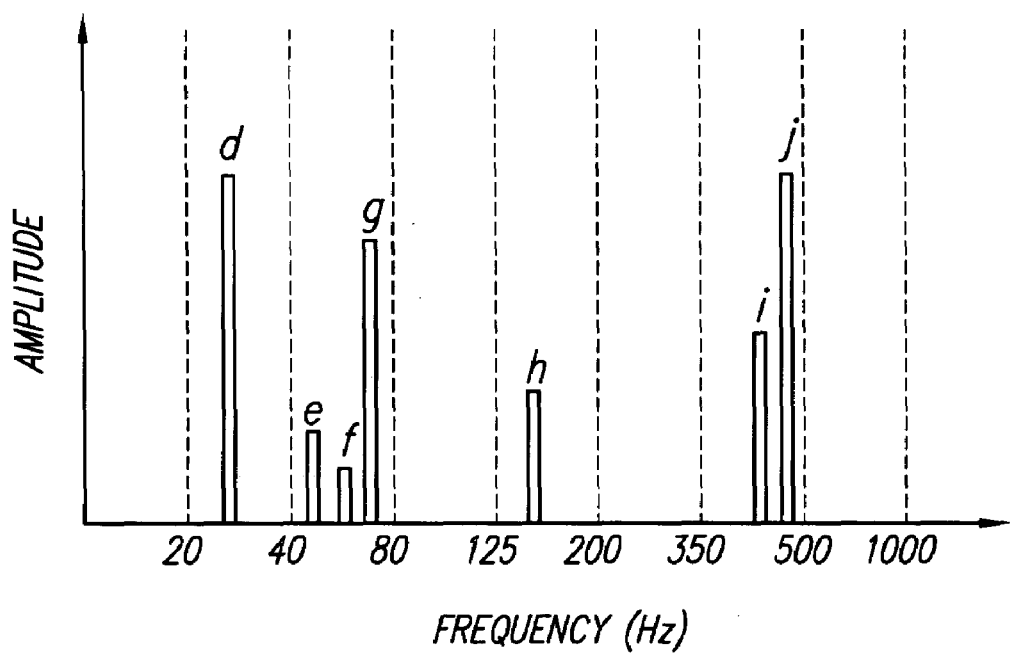
FIG. 2B shows a graph depicting eight frequency bands or windows with dominant FTS components d, g, h, and j.

FIG. 2B provides an example of an eight-channel system in which the sound frequency spectrum, from 0 to 1 kHz, is divided into eight frequency bands. Dominant FTS components shown are d, g, h, and j. These dominant FTS components are identified and captured by the system. Minor peaks e, f and i are discarded or not identified. In such an eight-channel system, there can be at least eight electrodes in the electrode array, each electrode representing one channel. When more frequency bands are used to capture more FTS, the resolution of the stimulation system is enhanced.

It can be appreciated that higher resolution can be obtained by having more channels, for example, using sixteen different channels employing a sixteen electrode array placed in-line or approximately in-line on a stimulation lead. There is, nevertheless, loss of information in such a system because, while the dominant FTS component is identified within a single frequency window, the conventional stimulation system does not further attempt to identify the exact FTS components within a frequency band and then convey that precise FTS information accurately to a corresponding location on the cochlea. This limitation is inherent in conventional cochlear stimulation systems because each electrode is placed in a fixed location with respect to the electrode array and, when the array is implanted, each electrode is fixed with respect to the cochlea. As a result, the FTS information of the incoming sound cannot be delivered to the proper cochlear locations, even if the precise FTS components are known.

FIG. 3A shows a diagram of a conventional CIS system. The system includes an envelope extractor and CIS carrier 30 and at least one electrode E1. This system is not capable of delivering FTS information to the nerves as it is limited by the physical placement of the electrodes.

FIG. 3B shows, in accordance with the present invention, a block diagram of a cochlear stimulation system which captures the FTS information in the auditory stimulation signals and conveys this information spatially (spectrally) to the nerves in the cochlea. The system of the present invention includes: (a) an FTS analyzer/estimator 35; and (b) a current navigator 40 for "current steering" to precisely direct the perceived stimulation to spatial locations on the cochlea that correspond to the FTS captured by the FTS analyzer. The task of the FTS analyzer is to estimate the dominant FTS components in each frequency band as, for example, shown previously in FIG. 2B. Each dominant FTS component is then linearly added to the carrier (frequency) signal obtained from the envelope extractor 30 by the current navigator 40 which processes and spatially directs the presentation of stimuli such that the peak of the excitations will be at the cochlear locations that correspond to the FTS components in each frequency band.

It can be seen from the block diagrams of FIGS. 3A and 3B that both the system of the present invention (FIG. 3B) and a conventional, cochlear stimulator system (FIG. 3A) includes an envelope extractor 30 for providing the carrier signal, and a linear array of m electrodes, $E_1, E_2 \ldots E_m$, which are 50, 50', and 50", respectively.

The present invention may further provide an FTS analyzer 35 which determines the precise, dominant FTS component within a frequency band. Assuming a stimulation system which has eight frequency bands, the FTS analyzer 35 determines the dominant FTS component within each frequency band. The dominant FTS component within each band is identified and the other minor FTS components within a band are generally discarded.

Figure 4:
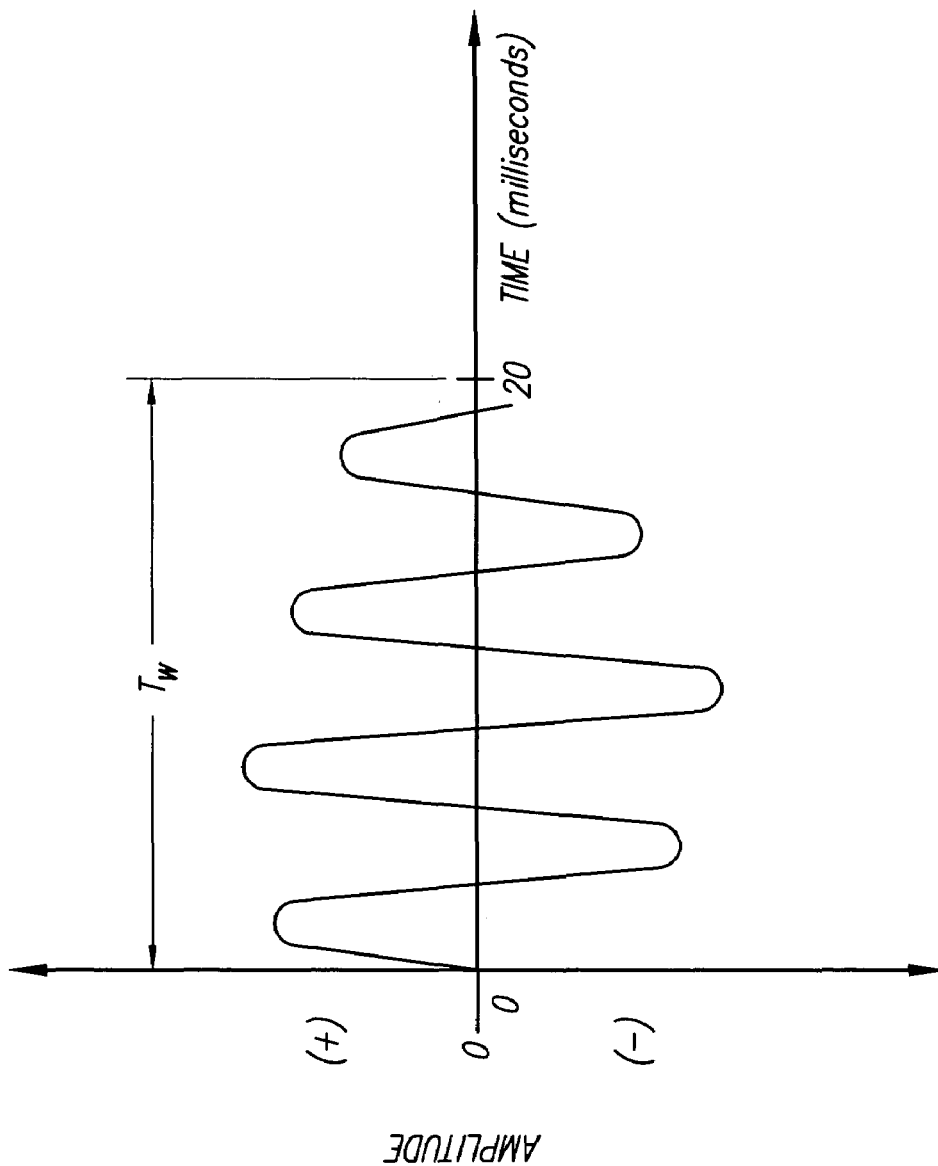
FIG. 4 shows, in accordance with the present invention, a depiction of a filter output which is one frequency band, wherein the dominant FTS component is calculated by averaging the intervals between zero crossings of the curve or counting the number of zero crossings of a curve and averaging the result.

FIG. 4 shows a graph, in accordance with the present invention, which illustrates a specific method for determining a dominant FTS component within a frequency band. The graph shows a time window, $T_W$, of 20 milliseconds looking at sounds within a frequency band of 125 to 250 Hz. One method for calculating the dominant FTS component (accomplished, for example, by the FTS analyzer) is to average the time intervals in the zero crossings within a time window. The peak FTS estimate is simply 1 over the average time interval. A selected time window of between about 10 to 100 milliseconds may be used to smooth the estimate so that stimulation is not perceived as noisy. A software program may be incorporated into the FTS analyzer or another part of the system to make the necessary calculations.

A second, alternative method, accomplished, for example, by the FTS analyzer, is to count zero crossing of the sound waves in a predetermined time window. The number of crossings is divided by the duration of the time window to achieve the frequency estimates. If both positive and negative going crossings are counted (in this case seven), then this zero crossings number is further divided by 2. Sufficiently accurate estimates can be achieved with a pre-determined time window that is at least 10 milliseconds long and preferably between about 10 to 100 milliseconds. A software program may be incorporated into the FTS analyzer or another part of the system to make the necessary calculations.

Another alternative method for determining the dominant FTS component is somewhat more sophisticated and employs a Fast Fourier Transform to precisely deconstruct the fundamental frequency components in a particular incoming sound. The dominant FTS component in a frequency band should be sustained over a pre-determined time duration of about between 10 to 100 milliseconds. A formant tracker, which can identify the dominant FTS components in a frequency band can be employed. Generally, because employing Fast Fourier transforms involves more involved processing algorithms than merely counting zero crossings, a software program will be necessary and specialized hardware may also be needed. Such a software program may be incorporated into the FTS analyzer or in another part of the system. A hardware and software implementation that uses a Fast Fourier Transform is expected to require greater processing power and use of the device's stored energy than a method in which only zero crossings are detected. Nevertheless, such a system, if cumbersome to implement at present, will become more easy to implement in the future, as processing capability continues to increase, while energy use decreases.

Once the specific, dominant FTSs in each of the frequency windows are identified, these must be conveyed spatially (spectrally) on the cochlea. Conventional stimulation systems do not convey the precise, dominant FTS components because the electrodes are fixed on the cochlea at specific locations. One strategy for escaping this limitation is to increase the number of electrodes and thereby decrease the inter-electrode spacing. However, such a strategy can only be carried to a limited extent, because at some point, increasing the number of electrodes does not always improve spatial precision in stimulating the nerves on the cochlea. The electrical field gradient around a single stimulating electrode has an inherent, spatial imprecision. There is a fixed, ceiling number of discrete electrodes for each type of electrode, beyond which, little improvement in spatial resolution will be seen.

The present invention may, in one embodiment, use sixteen electrodes placed in an in-line or approximately in-line arrangement on a stimulation lead. "In-line," as used herein, means in a straight line. The present invention, however, frees itself of limitations usually imposed by using a fixed number of electrodes and fixed placement of the electrodes on a cochlear place by employing a current navigator 40 which can direct current between fixed electrode locations. In particular, in the present invention, current field steering is achieved by employing the concept of "virtual" channels/electrodes. Virtual electrodes may be implemented by stimulating two or more electrodes in an electrode array to thereby produce a resulting stimulation current field that appears to emanate from a virtual electrode which is located somewhere between two physical electrodes.

The present invention uses a current navigator 40 to process the dominant FTS component information and non-simultaneously deliver stimuli through at least two electrodes in order to precisely steer perceived stimulation to the desired spatial location in the cochlea. By employing the concept of virtual electrodes, the perceived spatial (audio) frequency can more accurately reflect the dominant FTS component within a frequency band. In contrast, with conventional cochlear stimulation, disadvantageously, the frequency representation delivered to an electrode is necessarily a fixed, spacial frequency which is dependent on the pre-determined position of an electrode on the cochlea.

Figure 5A:
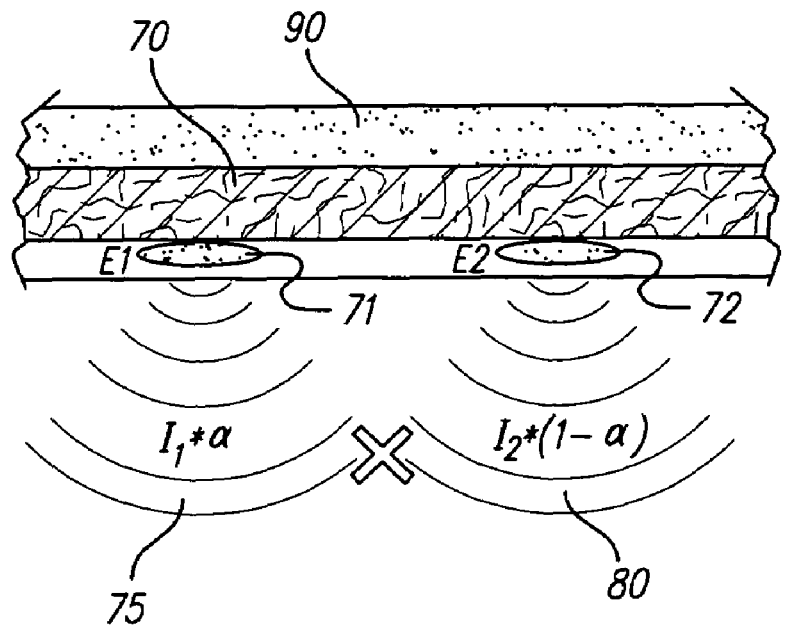
FIG. 5A provides an example of a virtual stimulation channel provided with a two electrode system for steering the current field.
Figure 5B:
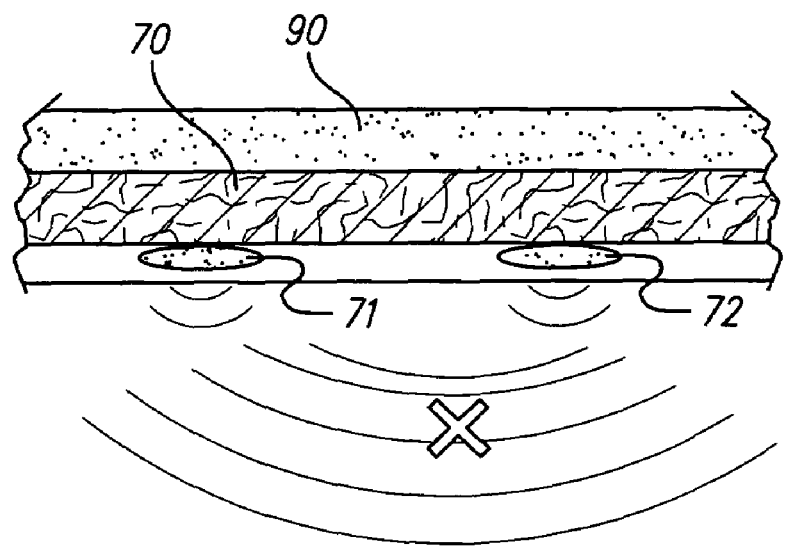
FIG. 5B provides another view of the same pair of electrodes in FIG. 5A, but with unequal current outputs between the two electrodes which skews the position of the highest intensity current field.

FIGS. 5A and 5B provide one example of implementing spatial current steering when two adjacent (cathodes) electrodes 71, 72 are concurrently activated. The use of simultaneously delivered stimulation is the subject of a separate, pending U.S. patent application Ser. No. 10/712,078, filed 13 Nov., 2003, which application is herein incorporated by reference in its entirety. A lead carrier 70 having the electrodes 71, 72, when properly sized, can be placed into the one of the chambers of the cochlea, such as the scala typmpani 90, and abutted against either a medial or the modiolar wall. At any given time, $I_1 * \alpha$ is applied to the first electrode 71, and $I_2 * (1-\alpha)$ is applied to a second, usually adjacent, electrode 72. Here, $I_1$ and $I_2$ represent current stimulation amplitudes and $\alpha$ is the fractional index (between 0 and 1) of the amplitude of $I_1$, relative to the amplitude of $I_2$. $I_1$ and $I_2$ are two pulse stimulus amplitudes such that, when presented on a first electrode 71 and a second electrode 72, respectively, have equal perceived loudness. The perceived loudness of a stimulation is determined by both its pulse amplitude and its rate of repetition (pulses per second).

The use of these two different values, $I_1$ and $I_2$, provides a calibration adjustment since placement of discrete electrodes is imprecise relative to target nerves and stimulation thresholds vary greatly between individual electrodes based on a number of factors. One of those factors is anatomical abnormalities in a patient in which some nerve bundles have died and, thus, particular areas of the cochlea may require more stimulation current to produce a given, perceived level of sound intensity.

By adjusting $\alpha$, the peak excitation point can be spatially moved within the cochlea somewhere between the natural peak of the first electrode ($\alpha=0$) and the natural peak of the second electrode ($\alpha=1$). As shown in FIG. 5A, when $I_1 * \alpha$ and $I_2 * (1-\alpha)$ are approximately equal, the two fields 75 and 80 combine to provide a point of highest field strength somewhere between the two electrodes 71 and 72, depicted as point "X." As shown in FIG. 5B, the point X can be shifted more towards one electrode, e.g., electrode 72, by varying the relative values of $I_1 * \alpha$ and $I_2 * (1-\alpha)$.

The value of $\alpha$ can be computed from the FTS analyzer/estimator 35 using the formula: $\alpha = \log\{F_{est}(t)/F_L\}/\log\{F_H/F_L\}$, where $F_{est}(t)$ is the current peak frequency estimate, and $F_H$ and $F_L$ are the low and the high frequency limits of a single frequency band, respectively. The estimator processing software can set $I_1$ and $I_2$ to zero, if $\alpha$ is either larger than 1 or less than 0.

The above example provides a two electrode example of a virtual electrode/channel, in which the electrodes provide current simultaneously. It can be appreciated that three or more electrodes may be selected to interact together to provide directed stimulation. In the two electrode example, both electrodes are cathodes and therefore operating in a monopolar electrode configuration. It is also possible that one or more electrode may function as return anodes, thereby operating in a bipolar electrode configuration. A tripolar electrode arrangement is possible, wherein the middle electrode is an anode and the two outer electrodes are cathodes, or vice-versa. The concept of current steering using delivery of concurrent stimuli at multiple electrodes has been disclosed, for example, in U.S. Pat. Nos. 6,052,624 and 6,393,325, both of which are herein incorporated by reference in their entireties.

In accordance with the present invention, it is also possible to implement virtual electrodes using non-simultaneously presented stimulation. That is, stimuli are presented in rapid sequence, one after the other, at two or more electrodes.

FIG. 6A shows a representation of an electrode array having five electrodes E1, E2, E3, E4 and E5. The electrode array may be substantially as shown and described in U.S. Pat. No. 4,819,647 or 6,129,753. Both patents are herein incorporated by reference. As shown in FIG. 6A, the top of the horizontal line represents the spectral (spatial) frequency. Point A on the horizontal line indicates the dominant sound frequency evoked by stimulating electrode E1 alone. An activation curve is represented around E1 and, as shown in FIG. 6B, an activation curve is also represented around E2. Point C in the upper horizontal line, as shown in FIG. 6B, indicates the sound frequency that would be evoked when electrode E2 is stimulated alone and point B represents the resulting intermediate spatial frequency that is achieved through non-simultaneous stimulation of E1 and E2. To achieve stimulation steering with non-simultaneous stimulation, E1 provides a first stimulus S1, and immediately thereafter, E2 delivers a stimulus S2.

Figure 6C:
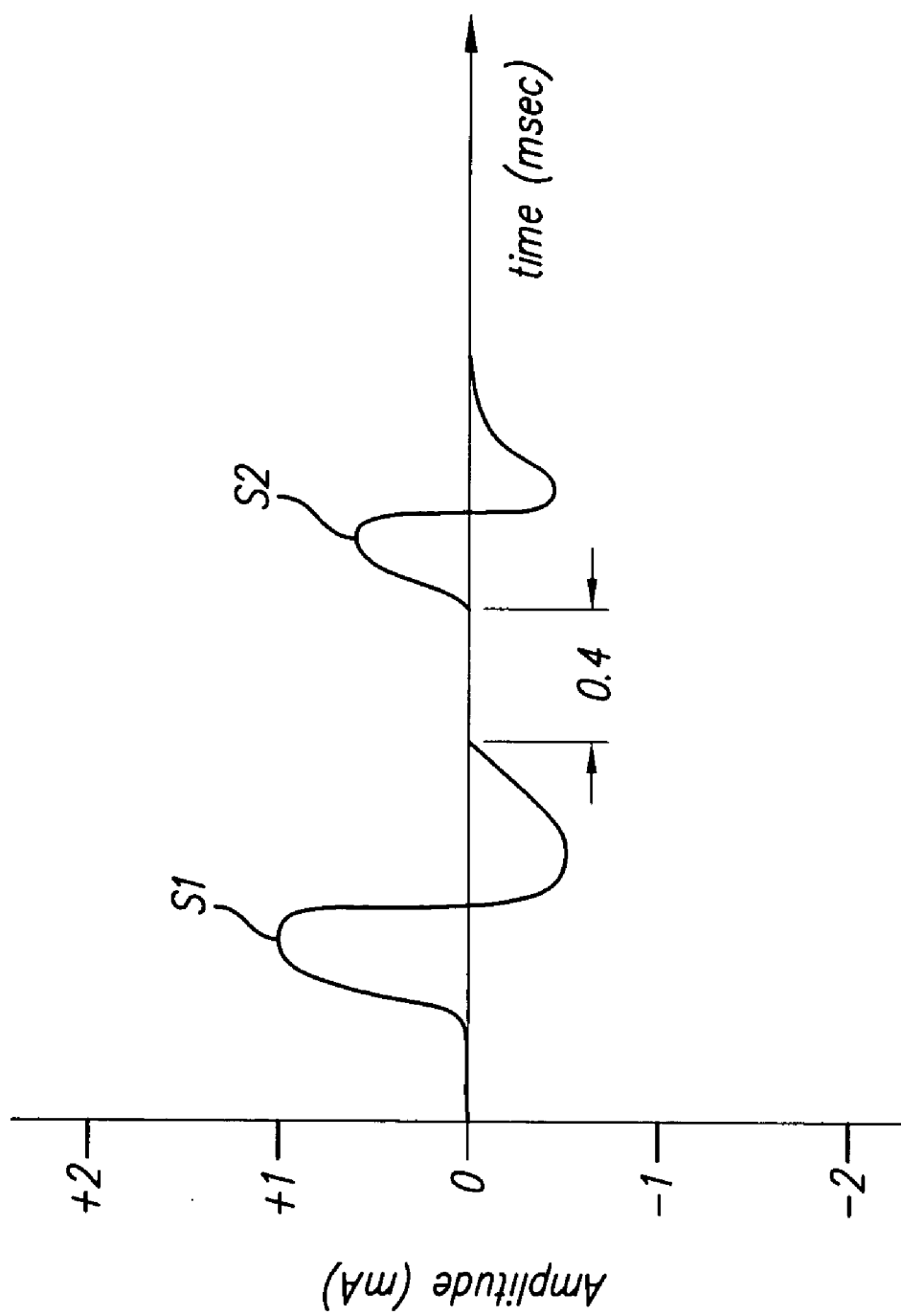
FIG. 6C shows a time representation of two bi-phasic stimuli that are applied in quick succession, first at E1 and then at E2.

FIG. 6C shows a representation of bi-phasic stimulus pulses S1 and S2 that are non-simultaneously delivered at E1 and E2, respectively. The effective stimulation point can be chosen spatially somewhere between the physical locations of E1 and E2 by varying the amplitudes of S1 and S2. The delivery of S2 after S1 should be within the neural refractory period of the target nerve, which is typically less than 1 millisecond and, more preferably, less than 0.4 milliseconds.

Small differences in energies between S1 and S2 can produce large shifts in the perceived sound frequencies. Such shifts in sound frequency can be somewhere between that which is normally perceived when E1 delivers stimulus S1 alone or when E2 deliver a stimulus S2 alone. (See, McDermott et al., Pitch Ranking with Nonsimultaneous Dual-Electrode Electrical Stimulation of the Cochlea, J. Acoust. Soc. Am., Vol. 96, No. 1, July 1994.)

The physiological mechanism for this resulting perceived frequency shift is not entirely clear. The first pulse, S1, may sensitize a nerve or, alternatively, cause charge to be "stored" within a nerve, although at a sub-threshold level. The second stimulus pulse, S2, provides enough additional charge at the target nerve to reach a supra-threshold level and causes the sensitized nerve to fire. S2 must occur within the refractory period of the target nerve which is usually less than about 1 millisecond. This neural refractory period determines the upper limit of the maximum time delay between two successive stimulus pulses S1 and S2, beyond which upper limit the perceived frequency shift will not occur.

This non-simultaneous stimulation for implementing virtual electrodes is not as energy efficient as simultaneous delivery of current at two electrodes to implement virtual electrodes. In the latter method, there is a true summing of two stimulus currents SC1 and SC2 to create a virtual electrode. In the former, non-simultaneous stimulation method, however, there is no summing of currents, and the stimulation currents S1 and S2, are much larger than SC1 and SC2, respectively. Moreover, small differences in magnitudes between S1 and S2 result in large perceptual frequency shifts. For example, there can be a large frequency shift between S1=60 db, S2=58 db and S1=60, S2=61 db.

The non-simultaneous stimulation method of the present invention employs "steering" and virtual electrodes between two physical electrodes. The method is particularly important in implementing the current navigator in a stimulator system which does not have independent control of stimulus from each electrode. In such a system, the only method to effect virtual electrodes, assuming the system is capable of delivering two stimuli at two electrodes in a sufficiently small time window, is through non-simultaneous stimulation. Thus, stimulation navigation may be advantageously accomplished even if the system hardware does not permit delivery of stimulus current to only one electrode at a time.

It is emphasized that the method of the invention, as represented in FIG. 3, is not dependent on the use of particular implementations of a FTS estimator and the particular current navigator. Other embodiments of FTS analyzers/estimators or current navigators may be used with the present invention other than those specific embodiments which have been disclosed.

It is further emphasized that the present method can be used in conjunction with other stimulation ideas including use of an M of N stimulation strategy. An M of N strategy is a stimulation strategy in which only M number of channels or electrodes are stimulated in one time interval of the N total available channels or electrodes. M is smaller than N, and both are whole numbers. Preferably, N is between 8 and 16 channels (or electrodes). Virtual electrodes may be used in such an M of N stimulation system, provided that at least two electrodes are used for stimulation, e.g., M is at least 2.

While the invention herein disclosed has been described by means of specific embodiments and applications thereof, numerous modifications and variations could be made thereto by those skilled in the art without departing from the scope of the invention set forth in the claims.

What is claimed is:

1. A cochlear stimulation system for capturing and delivering fine time structure (FTS) in incoming sounds, the system comprising:
   an electrode array, having a multiplicity of electrodes for placing into the cochlea;
   a stimulator having a multiplicity of stimulation channels connected to the electrode array, said each channel represented by a window or band of frequencies;
   an envelope extractor for extracting a slowly varying frequency envelope in the incoming sound;
   an FTS analyzer for estimating the FTS information within a frequency band, the analyzer contained within the stimulator; and
   a current navigator, for using the identified dominant FTS component at each band of frequency and for steering the stimulation to each point of the cochlea that spatially corresponds to the identified dominant FTS component,
   wherein the current navigator employs non-simultaneous stimulation, such that a first stimulus at a first electrode is followed immediately by a second stimulus at a second electrode, thereby employing virtual electrodes.

2. The system of claim 1, wherein the number of stimulation channels is sixteen.

3. The system of claim 2, wherein the electrode array has a multiplicity of sixteen electrodes, situated approximately in-line.

4. The system of claim 1, wherein the lead is sized to be placed inside the scala tympani.

5. The system of claim 1, wherein the FTS analyzer includes a software that extracts the number of zero-crossings in a pre-determined time interval to calculate the dominant FTS component in a frequency band.

6. The system of claim 5, wherein the pre-determined time interval is at least about 10 milliseconds.

7. The system of claim 1, wherein the FTS analyzer includes a software that employs Fast Fourier Transform to deconstruct the incoming sound, within a predetermined time interval, into dominant FTS components that are located in various frequency bands.

8. The system of claim 7, wherein the pre-determined time interval is at least about 10 milliseconds.

9. The system of claim 1,
   wherein the current navigator is capable of linearly adding the carrier frequency and the dominant FTS component provided by the FTS analyzer.

10. The system of claim 1, wherein the current navigator includes an M of N stimulation system.

11. A cochlear stimulation method for capturing and delivering FTS in incoming sounds, wherein the stimulation is provided by a multiplicity of electrodes in an electrode array connected to a multi-channel stimulator, the method comprising:
    analyzing the incoming sounds within frequency windows or bands, each frequency band representing one channel;
    extracting the slowly varying frequency carrier component of the incoming sound in each frequency band with an envelope;
    estimating the dominant FTS component using an FTS analyzer;
    adding the dominant FTS component to the carrier component to provide a precise corresponding spatial location on the cochlea; and
    steering the stimulation current to the precise spatial location on the cochlea using a current navigator,
    wherein stimulation steering is accomplished with non-simultaneous stimulation, such that a first stimulus is delivered by a first electrode and followed immediately by a second stimulus delivered by a second electrode, thereby employing virtual electrodes.

12. The method of claim 11, wherein the number of stimulation channels is sixteen.

13. The method of claim 12, wherein the electrode array has a multiplicity of sixteen electrodes, situated approximately in-line.

14. The method of claim 11, further comprising:
    placing the electrode array inside the scala tympani.

15. The method of claim 11, wherein estimating the dominant FTS component is accomplished by using software in the FTS analyzer that extracts the number of zero-crossings in a pre-determined time interval.

16. The method of claim 15, wherein the pre-determined time interval is at least about 10 milliseconds.

17. The method of claim 11, wherein estimating the dominant FTS is accomplished by an FTS analyzer that deconstructs incoming sounds in a predetermined time interval, employing Fast Fourier Transformation.

18. The method of claim 17, wherein the pre-determined time interval is at least about 10 milliseconds.

19. The method of claim 11, wherein the step of adding the FTS information to the carrier is accomplished by linearly adding the two.

20. The method of claim 11, wherein the stimulation method includes an M of N stimulation strategy.

21. The method of claim 11, wherein estimating the dominant FTS is performed by taking the average of the intervals between zero-crossings.

* * * * *